US010421739B2

(12) United States Patent
Mainkar et al.

(10) Patent No.: US 10,421,739 B2
(45) Date of Patent: Sep. 24, 2019

(54) PROCESS FOR THE PREPARATION OF NICOTINE

(71) Applicant: Council of Scientific & Industrial Research, New Delhi (IN)

(72) Inventors: Prathama Satyendra Mainkar, Hyderabad (IN); Kondepudi Sugnana Sunder, Hyderabad (IN); Togapur Pavan Kumar, Hyderabad (IN); Srivari Chandrasekhar, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/068,464

(22) PCT Filed: Jan. 6, 2017

(86) PCT No.: PCT/IN2017/050007
§ 371 (c)(1),
(2) Date: Jul. 6, 2018

(87) PCT Pub. No.: WO2017/119003
PCT Pub. Date: Jul. 13, 2017

(65) Prior Publication Data
US 2019/0016699 A1    Jan. 17, 2019

(30) Foreign Application Priority Data

Jan. 8, 2016 (IN) .............................. 201611000697

(51) Int. Cl.
*C07D 401/04* (2006.01)
(52) U.S. Cl.
CPC ................. *C07D 401/04* (2013.01)
(58) Field of Classification Search
CPC .................................................. C07D 401/04
See application file for complete search history.

(56) References Cited

U.S. PATENT DOCUMENTS

| | | | |
|---|---|---|---|
| 4,321,387 A | 3/1982 | Chavdarian et al. | |
| 4,442,292 A | 4/1984 | Edwards, III | |
| 4,452,984 A | 6/1984 | Edwards, III | |
| 8,389,733 B2 | 3/2013 | Divi et al. | |
| 2014/0031554 A1 | 1/2014 | Tian et al. | |

FOREIGN PATENT DOCUMENTS

| | | | |
|---|---|---|---|
| EP | 2016954 | * | 1/2009 |
| EP | 2016954 A1 | | 1/2009 |
| EP | 2487172 A1 | | 8/2012 |

OTHER PUBLICATIONS

Polindara-Garcia, Org Biomol Chem, 2015, vol. 13, 9065-9071. (Year: 2015).*
Leete, J oRg Chem, vol. 37(26), Jan. 1972, 4465-4466. (Year: 1972).*
International Search Report and Written Opinion completed Mar. 27, 2017, pertaining to PCT/IN2017/050007 filed Jan. 6, 2017.
Langhals et al., "Eine Synthese von Nornikotin- und Nikotin-2-carboxamid" Liebigs Annalen Der Chemie, Jan. 1, 1983, pp. 330-333, Abstract.
Murahashi et al., "Tungstate-Catalyzed Oxidation of Secondary Amines to Nitrones, Alpha-Substitution of Secondary Amines via Nitrones", The Journal of Organic Chemistry, American Chemical Society etc., vol. 6, No. 55, Jan. 1, 1990, pp. 1736-1744.
DeTraglia et al., "Separation of D-(+)-Nicotine from a Racemic Mixture by Stereospecific Degradation of the L-(−) Isomer with Pseudomonas putida", Applied and Environmental Microbiology, vol. 39, No. 5, May 1980, pp. 1067-1069.
Aceto et al., "Optically Pure (+)-Nicotine from (±)-Nicotine and Biological Comparisons with (−)-Nicotine", Journal of Medicinal Chemistry, 1979, vol. 22, No. 2, pp. 174-177.
Leete et al., "Synthesis of Myosmine and Nornicotine, Using an Acyl Carbanion Equivalent as an Intermediate", J. Org. Chem., vol. 37, No. 26, Jan. 1, 1972, pp. 4465-4466.
Chavdarian et al., "Synthesis of Optically Active Nicotinoids", J. Org. Chem., 1982, 41, pp. 1069-1073.
Loh et al., "A novel reductive aminocyclization for the syntheses of chiral pyrrolidines: stereoselective syntheses of (S)-nornicotine and 2-(2'-pyrrofidyl)-pyridines", Tetrahedron Letters 40, 1999, pp. 7847-7850.
Dübon et al., "Enantioselective Syntheses of 2-Substituted Pyrrolidines from Allylamines by Domino Hydroformylation-Condensation: Short Syntheses of (S)-Nicotine and the Alkaloid 225C", Synlett 2009, No. 9, pp. 1413-1416.
Huang et al., "A New and Efficient Approach to the Synthesis of Nicotine and Anabasine Analogues", J. Heterocyclic Chemistry, 46, 2009, pp. 1252-1258.
Baxendale et al., "Synthesis of nornicotine, nicotine and other functionalised derivatives using solid-supported reagents and scavengers", J. Chem. Soc., Perkin Transactions I, 2002, pp. 143-154.
Bashiardes et al., "Synthesis of Nicotine and Diverse Analogues Using Intramolecular [3+2] Cycloaddition", Synlett 2009, No. 15, pp. 2497-2499.

* cited by examiner

*Primary Examiner* — D Margaret M Seaman
(74) *Attorney, Agent, or Firm* — Dinsmore & Shohl, LLP

(57) ABSTRACT

The present invention relates to a process for the preparation of racemic nicotine from 3-pyridylaldehyde using a one-pot or step-wise method. The process comprises the following steps: Stetter reaction, reduction-cyclization and methylation.

9 Claims, 1 Drawing Sheet

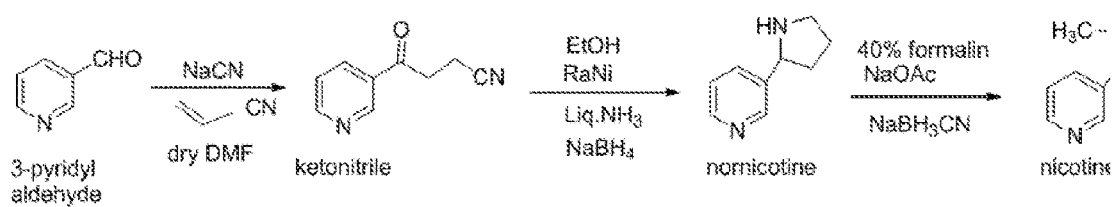
Scheme 1

PROCESS FOR THE PREPARATION OF NICOTINE

FIELD OF THE INVENTION

The present invention relates to a process for the synthesis of racemic nicotine. Particularly, the present invention relates to a process for the preparation of nicotine from 3-pyridylaldehyde in one-pot or a step-wise process.

BACKGROUND OF THE INVENTION

Nicotine, mainly found in tobacco and other nightshade family of plants is essentially a parasympathomimitic alkaloid and is a stimulant drug. Nicotine is directly related to smoking of tobacco, as it results in nicotine dependence and is habit forming. Smoking is not only habit forming, it may also lead to the diseases of lungs including malignant growth and harmful effects of smoking are well recognized globally. Inspite of knowing these serious effects, unfortunately habitual smokers cannot overcome their dependency and is still habit forming. In early 1990s nicotine replacement therapy was widely promoted by World Health Organization to overcome the dependency on cigarette and to give-up smoking. In this direction, products containing minimal quantities of nicotine were developed and promoted as substitutes for traditional smoking agents like cigarettes etc. Nicotine was also found to be a promising and effective drug, which is therapeutically used for treating Alzheimer's disease, schizophrenia, Parkinson's syndrome, Tourette's syndrome, attention deficit disorder, depression etc.

The natural nicotine is levogyric and is chemically denoted as (S)-3-(1-methyl-2-pyrrolidinyl)pyridine. Tobacco is the prime source for nicotine and the nicotine isolated from tobacco contains other related alkaloids and degradation products as impurities. Therefore the impurities present in natural nicotine are not fixed always and may vary depending on the geographical origin and climatic conditions etc. With these features, the natural nicotine always contains closely related impurities and which are very difficult to remove. The pharmacopoeias also recognize these variations and have different limits for the impurities listed.

The racemic nicotine was also found to have similar pharmacological effect as that of natural nicotine. It is only slightly less potential, but has much lower toxicity than the natural nicotine. It is very much straightforward that, the nicotine obtained from synthetic process is expected to be free from the impurities that are present in the natural nicotine. By synthetic method, one can prepare optically pure as well as racemic versions of nicotine from lab scale to industrial production. The racemic synthesis is a simpler process compared to the enantioselective synthesis, which is difficult to practice at the industrial scale. Therefore, synthesis of (R,S)-nicotine followed by resolution is the best process to explore. The resolution of racemic nicotine is well documented in the literature using d-tartaric acid (J. Med. Chem. 1979, 22, 174-177) or enzymatic resolution (Applied and Environmental Microbiology, 1980, 39, 1067-1069).

Till date, several synthetic processes for the nicotine are reported in the literature, some of these are for the synthesis of (S)-nicotine (J. Org. Chem. 1982, 41, 1069-1073; Tetrahedron Letters, 1999, 40, 7847-7650; Synlett 2009, 9, 1413-1416) and some others are for racemic nicotine. A racemic synthesis of nicotine starting from pyrrolidine (Journal of Organic Chemistry, 1990, 55, 1736-44) could be carried out in a four step reaction sequence. The use of tert-butyl lithium and low reaction temperatures are the limitations for this process to be effective at industrial production. Another synthesis of nicotine starting from nicotinic acid (Perkin Transactions I, 2002, 143-154) also involves a four step reaction sequence and in this process the use of Grignard reagent limits its usage at industrial scale.

The other reported methods for the synthesis of racemic nicotine are (a) Synlett, 2009, 2497-2499; (b) Journal of Heterocyclic Chemistry, 2009, 46, 1252-1258; (c) U.S. Pat. No. 8,389,733 (d) U.S. Pat. No. 8,884,021. Though, several of these methods are practical at laboratory level, only few of them are useful at industrial production. Most of these reported methods are difficult to be practiced at the industrial production due to one or more of the following factors: (a) expensive reagents and/or raw materials (b) uneven temperature and/or reaction times (c) multi-step process (d) operationally difficult reaction conditions/parameters.

OBJECTIVE OF THE INVENTION

Main objective of the present invention is to provide an efficient process for the synthesis of racemic nicotine.

Another objective of the present invention is to provide a process, that could be carried out in one-pot or step-wise manner for the preparation of nicotine starting from 3-pyridylaldehyde.

BRIEF DESCRIPTION OF THE DRAWINGS

FIG. 1: Scheme 1: represents process steps for the synthesis of racemic nicotine.

SUMMARY OF THE INVENTION

Accordingly, present invention provides a process for the preparation of racemic nicotine comprising the steps of:
i. mixing 3-pyridylaldehyde and acrylonitrile in presence of dimethylformamide and sodium cyanide using Stetter reaction at a temperature in the range of 30-40° C. to obtain ketonitrile;
ii. reducing the ketonitrile as obtained in step (i) in presence of reducing reagent in alcoholic solvent followed by cyclisation to obtain nornicotine;
iii. methylating of nornicotine as obtained in step (ii) using sodium acetate, formalin, and sodium cyanoborohydride in water followed by purification by column chromatography to obtain the pure racemic nicotine, optionally isolating and purifying intermediate compounds obtained in step (i) and (ii).

In yet another embodiment of the present invention, alcoholic solvent in reaction step (ii) is selected from ethyl alcohol or methyl alcohol.

In still an embodiment of the present invention, alcoholic solvent in reaction step (ii) is ethyl alcohol.

In yet another embodiment of the present invention, the reducing reagent in reaction step (ii) is selected from the group consisting of RaNi, sodium borohydride or mixture thereof.

The process as claimed in claim 1, wherein eluent for column chromatography in step (i) is ethylacetate and hexane.

In yet another embodiment of the present invention, eluent for column chromatography in step (ii) and (iii) is chloroform and methanol.

In yet another embodiment of the present invention, said process is carried out by one-pot or stepwise operation.

In yet another embodiment of the present invention, the one-pot operation is carried-out without isolation and purification of reaction intermediates formed during each stage.

In yet another embodiment of the present invention, the stepwise operation is carried-out with isolation and purification of reaction intermediates formed during each stage.

DETAILED DESCRIPTION OF THE INVENTION

Present invention provides a highly effective process for the synthesis of racemic nicotine.

This process could be operated in a one-pot or step-wise manner to achieve the racemic nicotine in high yields and purity. The newly developed process starts from 3-pyridylaldehyde as the key raw material and comprises of following operations: Stetter reaction, reduction-cyclisation and methylation as illustrated in scheme 1 (FIG. 1).

The present process can be performed easily and is a very economic strategy which is most suitable for industrial scale. Both the process types, i.e one-pot and step-wise will yield the racemic nicotine in similar yields and purity except for the variation in workup methods. In a one-pot operation, the three process steps were carried out in one reaction setup without any specific purification/isolation step and the final product nicotine is characterized for purity and yield. While, the step-wise process is carried out in three different reaction setups and involves purification and characterization of the individual reaction product at each stage.

The present process for the preparation of racemic nicotine as illustrated in scheme 1 (FIG. 1) is described as follows. This process is the most convenient and simple method involving three step reaction sequence starting from 3-pyridylaldehyde comprising of following steps:
  i. The first reaction of the process is Stetter reaction using 3-pyridylaldehyde and acrylonitrile in presence of dimethylformamide as reaction solvent and sodium cyanide as the reagent at 30-40° C., which gives the ketonitrile in good yield.
  ii. The second reaction in the process is reduction-cyclization-reduction of the ketonitrile in presence of reducing reagents in alcoholic solvents leading to the formation of nornicotine in high yields.
  iii. While the third reaction is methylation of nornicotine using sodium acetate, formalin, and sodium cyanoborohydride in water to yield in crude racemic nicotine.
  iv. Finally, the pure racemic nicotine is obtained by purification of the above crude racemic nicotine.

The synthesis of racemic nicotine can be performed in a one-pot operation, wherein all the three reactions; Stetter reaction, reduction-cyclisation and methylation are carried out one-after the other without isolating the intermediate formed during each reaction step.

In one-pot operation process, the final product-racemic nicotine formed is purified by column chromatography or distillation and the yield of the product obtained is 73%.

The synthesis of racemic nicotine can also be performed in step-wise manner, wherein the reaction products resulting from each individual reaction are purified and characterized.

In the process of step-wise preparation of nicotine, all the three steps are high yielding with an yield of above 70%.

The alcoholic solvent used in second reaction, reduction-cyclization is ethyl alcohol.

In the synthesis of racemic nicotine by step-wise manner, the completion of the second reaction could be monitored by thin layer chromatography.

In the synthesis of racemic nicotine by step-wise manner, the purification procedures are distillation, filtration, recrystallization or simple solvent extraction or chromatography.

The solvent used for extraction or crystallization or purification is selected from methanol, ethylacetate, 2-propanol or chloroform.

EXAMPLES

Following examples are given by way of illustration and therefore should not be construed to limit the scope of the invention.

Example 1

Preparation of 4-oxo-4-(pyridin-3-yl)butanenitrile

A finely powdered NaCN (250 mg, 5 mmol) in 25 mL dry DMF was vigorously stirred at 35° C. for 15 min., and was added 3-pyridaldehyde (5.5 g, 50 mmol) dropwise over a period of 30 min. To the resulting solution was then added acrylonitrile (2.61 g, 5 mmol) over 1 h and the resulting mixture was stirred for 3 h. Then, a drop of glacial acetic acid was added and stirred for 5 min. and the reaction mixture was treated with saturated ammonium chloride solution. The aqueous phase was extracted four times with chloroform and twice with ethylacetate. All the organic extracts were dried using sodium sulfate and concentrated under vacuo to give the residual cyano compound as oil. This crude residue is purified by silica gel column chromatography using ethylacetate and hexane as eluent and the product on further purification by recrystallization using 2-propanol yielded the product 4-oxo-4-(pyridin-3-yl)butanenitrile, as an orange solid (5.4 g, 70%).

IR (KBr): v 3361, 2937, 2249, 1691, 1587, 1420, 1257, 974, 703 cm$^{-1}$. $^1$H NMR (CDCl$_3$, 300 MHz): δ9.17-9.14 (m, 1H), 8.84-8.79 (m, 1H), 8.26-8.21 (m, 1H), 7.42-7.38 (m, 1H), 3.38-3.27 (m, 2H), 2.87-2.82 (m, 2H); ESI-MS: m/z 161 [M+H]$^+$.

Example 2

Preparation of 3-(pyrrolidin-2-yl)pyridine/nornicotine

The ketonitrile, 4-oxo-4-(pyridin-3-yl)butanenitrile (3 g, 18 mmol) was dissolved in absolute ethanol (30 mL) and liquid ammonia was condensed for 20 mL at −75 to −80° C. The complete reaction mixture is subjected to hydrogenation at 2 atm pressure in presence of RaNi (1.5 teaspoon quantity) for about 36 h. Reaction was monitored by TLC and after completion of the reaction, the reaction mixture was filtered through celite and then treated with sodium borohydride (850 mg, 1.5 equiv.) and refluxed for 1 h. Then, the reaction mixture was cooled and acidified with HCl and evaporated to dryness. Cold water was added and the resulting residue was made basic with 50% NaOH solution and extracted with dichloromethane, dried with sodium sulfite, concentrated in vacuo to give nornicotine. The crude sample was purified by column chromatography using chloroform and methanol as eluent to give pure nornicotine (2.0 g, 76%). IR (KBr): v 3253, 2930, 2855, 2248, 1580, 1427, 1250, 1079, 913, 741 cm$^{-1}$; $^1$H NMR (CDCl$_3$, 300 MHz): δ8.73-8.59 (m, 1H), 8.51-8.39 (m, 1H), 7.82-7.71 (m, 1H), 7.34-7.23 (m, 1H), 4.26-4.18 (m, 1H), 3.22-3.18 (m, 1H), 3.16-2.96 (m, 1H), 2.24-2.17 (m, 1H), 1.99-1.83 (m, 2H), 1.73-1.62 (m, 1H); ESI-MS: m/z 149 [M+H]$^+$.

Example 3

Preparation of 3-(1-methylpyrrolidin-2-yl)pyridine/nicotine

The nornicotine (1 g, 6.7 mmol) was dissolved in water (10 mL) and treated with sodium acetate to achieve pH 6. Then, formaldehyde (40% formalin-2 mL) and sodium cyanoborohydride (1 g, 15.9 mmol) was added to the reaction vessel and the resulting mixture is stirred for 45 min. The reaction mixture was cooled and made acidic with HCl (7-8 mL), aqueous phase was washed three times with diethyl ether (3×30 mL) and then made basic with 50% NaOH solution. Then, extracted four times with dichloromethane (4×50 mL) and the resultant organic phases were washed with brine, dried over sodium sulfate and concentrated in vacuo to give nicotine. The crude sample was purified by column chromatography using chloroform and methanol as eluent to give pure nicotine (0.8 g, 73%). IR (KBr): v 2925, 2841, 2239, 1417, 1136, 1059, 908, 732 cm$^{-1}$; $^1$H NMR (CDCl$_3$, 300 MHz): δ8.49-8.46 (m, 1H), 8.44-8.42 (m, 1H), 7.74-7.68 (m, 1H), 7.41-7.35 (m, 1H), 3.57-3.54 (m, 1H), 3.23-3.17 (m, 1H), 3.08-2.94 (m, 1H), 2.29-2.09 (m, 4H), 1.87-1.79 (m, 1H), 1.76-1.64 (m, 2H); ESI-MS: m/z 163 [M+H]$^+$.

Example 4

Preparation of 3-(1-methylpyrrolidin-2-yl)pyridine/nicotine

A finely powdered NaCN (250 mg, 5 mmol) in 25 mL dry DMF was vigorously stirred at 35° C. for 15 min., and was added 3-pyridaldehyde (5.5 g, 50 mmol) dropwise over a period of 30 min. To the resulting solution was then added acrylonitrile (2.61 g, 5 mmol) over 1 h and the resulting mixture was stirred for 3 h. Then, a drop of glacial acetic acid was added and stirred for 5 min. and the reaction mixture was treated with saturated ammonium chloride solution. The aqueous phase was extracted four times with chloroform and twice with ethylacetate. All the organic extracts were dried using sodium sulfate and concentrated under vacuo to give the residual cyano compound as oil. This compound was then directly dissolved in absolute ethanol (30 mL) and liquid ammonia was condensed for 20 mL at −75 to −80° C. The complete reaction mixture is subjected to hydrogenation at 2 atmospheric pressure in presence of RaNi (1.5 teaspoon quantity) for about 36 h. Reaction is monitored by TLC and after completion of the reaction, the reaction mixture is filtered through celite and then treated with sodium borohydride (850 mg, 1.5 equiv.) and refluxed for 1 h. Then, the reaction mixture is cooled and acidified with HCl and evaporated to dryness. Cold water was added and the resulting residue was made basic with 50% NaOH solution and extracted with dichloromethane, dried with sodium sulfite and concentrated in vacuo to give nornicotine. The crude nornicotine was dissolved in water (10 mL) and treated with sodium acetate to achieve pH 6. Then, formaldehyde (40% formalin-2 mL) and sodium cyanoborohydride (1 g, 15.9 mmol) was added to the reaction vessel and the resulting mixture is stirred for 45 min. The reaction mixture was cooled and made acidic with HCl (7-8 mL), aqueous phase was washed three times with diethyl ether (3×30 mL) and then made basic with 50% NaOH solution. Then, extracted four times with dichloromethane (4×50 mL) and the resultant organic phases were washed with brine, dried over sodium sulfate and concentrated in vacuo to give nicotine. The crude sample was purified by column chromatography to give pure nicotine (0.8 g, 73%). IR (KBr): v 2925, 2841, 2239, 1417, 1136, 1059, 908, 732 cm$^{-1}$; $^1$H NMR (CDCl$_3$, 300 MHz): δ8.49-8.46 (m, 1H), 8.44-8.42 (m, 1H), 7.74-7.68 (m, 1H), 7.41-7.35 (m, 1H), 3.57-3.54 (m, 1H), 3.23-3.17 (m, 1H), 3.08-2.94 (m, 1H), 2.29-2.09 (m, 4H), 1.87-1.79 (m, 1H), 1.76-1.64 (m, 2H); ESI-MS: m/z 163 [M+H]$^+$.

ADVANTAGES OF THE INVENTION

The various advantages of the present process are given below.

The present process serves as a highly efficient and scalable production method for the synthesis of racemic nicotine.

The advantage of the present invention is that the process could be operated in one-pot or step-wise method.

Another advantage of the present invention is the employment of simpler reaction parameters.

Isolation and/or purification of the products is straightforward.

This is an attractive and economic method for the production of racemic nicotine.

The racemic nicotine could be easily subjected to resolution by adopting the reported methods to obtain optically pure nicotine.

We claim:
1. A process for preparation of racemic nicotine comprising:
   i. mixing 3-pyridylaldehyde and acrylonitrile in presence of dimethylformamide and sodium cyanide using Stetter reaction at a temperature in the range of 30-40° C. to obtain ketonitrile;
   ii. reducing the ketonitrile as obtained in (i) in presence of a reducing reagent in alcoholic solvent followed by cyclisation to obtain nornicotine;
   iii. methylating of the nornicotine as obtained in (ii) using sodium acetate, formalin, and sodium cyanoborohydride in water followed by purification by column chromatography to obtain pure racemic nicotine, and
   optionally isolating and purifying intermediate compounds obtained in (i) and (ii).

2. The process as claimed in claim 1, wherein the alcoholic solvent in (ii) is selected from the group consisting of ethylalcohol and methylalcohol.

3. The process as claimed in claim 2, wherein the alcoholic solvent is ethyl alcohol.

4. The process as claimed in claim 1, wherein the reducing reagent in (ii) is selected from the group consisting of RaNi, sodium borohydride, and a mixture thereof.

5. The process as claimed in claim 1, wherein eluent for the column chromatography in (iii) is ethylacetate and hexane.

6. The process as claimed in claim 1, wherein eluent for the column chromatography in (iii) is chloroform and methanol.

7. The process as claimed in claim 1, wherein the process is carried out by one-pot or stepwise operation.

8. The process as claimed in claim 7, wherein the one-pot operation is carried-out without isolation and purification of reaction intermediates formed during each stage.

9. The process as claimed in claim 7, wherein the stepwise operation is carried-out with isolation and purification of reaction intermediates formed during each stage.

* * * * *